United States Patent [19]

Gaertner et al.

[11] 4,119,430

[45] Oct. 10, 1978

[54] N-(2-HYDROXYALKYL) DERIVATIVES OF N-PHOSPHONOMETHYLGLYCINE AND HERBICIDAL COMPOSITIONS CONTAINING SAME

[75] Inventors: Van R. Gaertner, Ballwin; Philip C. Hamm, Glendale, both of Mo.

[73] Assignee: Monsanto Company, St. Louis, Mo.

[21] Appl. No.: 798,043

[22] Filed: May 18, 1977

Related U.S. Application Data

[63] Continuation-in-part of Ser. No. 714,054, Aug. 13, 1976, Pat. No. 4,047,927.

[51] Int. Cl.$^2$ ............................................. A01N 9/36
[52] U.S. Cl. ............................................. 71/86; 260/932; 260/941; 260/502.5; 560/169; 560/170
[58] Field of Search ............ 71/86; 260/502.5; 560/169, 170; 260/932, 941

[56] References Cited

U.S. PATENT DOCUMENTS

| | | | |
|---|---|---|---|
| 3,453,301 | 7/1969 | Uhing | 260/502.5 X |
| 3,455,675 | 7/1969 | Irani | 71/86 |
| 3,548,038 | 12/1970 | Beck | 260/932 |
| 3,799,758 | 3/1974 | Franz | 71/86 |
| 3,835,000 | 9/1974 | Frazier et al. | 204/78 |
| 3,888,915 | 6/1975 | Alt | 260/502.5 |
| 3,910,969 | 10/1975 | Franz | 260/397.7 R |
| 3,927,080 | 12/1975 | Gaertner | 260/502.5 |
| 3,933,946 | 1/1976 | Gaertner | 71/86 X |

FOREIGN PATENT DOCUMENTS 2,360,711  6/1975  Fed. Rep. of Germany.

*Primary Examiner*—Joseph Paul Brust
*Attorney, Agent, or Firm*—Arnold H. Cole; Donald W. Peterson

[57] ABSTRACT

Certain N-(2-hydroxyalkyl) derivatives of N-phosphonomethylglycine have been found to be useful as herbicides for the treatment of undesired plants.

16 Claims, No Drawings

N-(2-HYDROXYALKYL) DERIVATIVES OF N-PHOSPHONOMETHYLGLYCINE AND HERBICIDAL COMPOSITIONS CONTAINING SAME

This application is a continuation-in-part of application Ser. No. 714,054, filed Aug. 13, 1976, now U.S. Pat. No. 4,047,927.

This invention relates to a class of chemical compounds which are derivatives of N-phosphonomethylglycine wherein the central nitrogen atom contains a 2-hydroxyalkyl substituent thereon. This class of compounds has been found to be useful as post-emergent herbicides for the treatment of undesirable plants.

U.S. Pat. No. 3,455,675 teaches the use of certain aminophosphonate compounds as herbicides for the destruction of undesired plants. These compounds require the presence of three acid groups attached to the nitrogen atom, each attachment being through an alkylene (or methylene) bridge. One or two of such acid groups must be phosphonic acid, and the remaining group or groups must be carboxylic acid (acetic acid). Further, U.S. Pat. No. 3,799,758 teaches that N-phosphonomethylglycine, and certain esters, amides and salts thereof, are useful as herbicides for the destruction of undesired plants. All of these compounds must contain a hydrogen atom on the nitrogen. In addition, U.S. Pat. No. 3,910,969 shows that N-phenylsulfonamido derivatives of N-phosphonomethylglycine are useful in the treatment of sugarcane to increase sucrose content. In U.S. Pat. No. 3,835,000, N-(2-hydroxyethyl)-N-phosphonomethylglycine is identified by formula as a starting material in a chemical process.

In accordance with the present invention, it has been found that certain N-(2-hydroxyalkyl) derivatives of N-phosphonomethylglycine, along with esters and salts thereof, can be employed as herbicides for the post-emergent treatment of undesired plants. The novel derivatives may be represented by the formula:

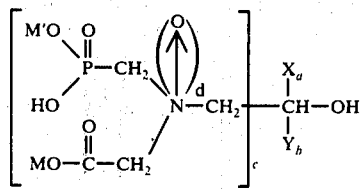

wherein X is selected from hydroxymethyl, lower alkoxymethyl and lower alkenoxymethyl, Y is selected from hydrogen, methyl and ethyl, M is selected from hydrogen, lower alkyl and alkali metal, M' is selected from hydrogen, lower alkyl, phenyl and alkali metal, $a$ and $b$ are independently zero or one, $c$ is one or two, and $d$ is zero or one, provided that the sum of $a+b+c$ must equal two, and $d$ must be one when $b$ is one. As employed herein, lower designates those radicals containing up to four carbon atoms in a straight or branched chain. The alkali metal salts defined by the above formula are especially preferred in the practice of the herbicidal methods hereinafter described.

A method for preparing compounds of this invention involves the reaction of a suitable epoxide with an alkali metal salt of N-phosphonomethylglycine. In those instances where $c$ is one, the two reactants can be employed in equimolar amounts although an excess of epoxide may be used to assist in driving the reaction to completion. In those instances where $c$ is two, the starting salt is employed in approximately a 2:1 molar ratio relative to the epoxide. The products obtained by the above reactions are in salt form, and, if desired, can be acidified by known procedures to give the corresponding free acids. These acids are stable at room temperatures, but will lactonize as temperatures are elevated. The N-oxides of said products are obtained by reaction with a suitable oxidizing agent.

The reaction is generally carried out at room temperature or below, and external cooling may be necessary due to exothermic temperature increases. The reaction should be carried out at a pH in the range of about 6 to 9.

The examples which follow will serve to further illustrate the preparation of specific individual compounds of the present invention.

EXAMPLE 1

The disodium salt of N-phosphonomethylglycine is prepared by treating a slurry of 16.9 grams (0.10 mole) of N-phosphonomethylglycine in 30 ml. of water with 16 grams (0.20 mole) of 50% aqueous sodium hydroxide. The hot solution is stirred and cooled in an ice bath to 5°–10° C.

To the disodium salt solution is added 8.1 grams (0.11 mole) of glycidol. The solution is then allowed to stir and warm overnight in the melting ice bath. To complete the reaction, a 2.0 gram portion of glycidol is added, and the solution is stirred at 22° C. The solution is allowed to stand for several days and is then rotoevaporated to dryness. The solid is then redried over potassium hydroxide pellets in a vacuum desiccator below 1 mm. Hg. There is obtained the disodium salt of N-(2,3-dihydroxy-1-propyl)-N-phosphonomethylglycine as a white, brittle foamed glass.

EXAMPLE 2

To a solution of the disodium salt of N-phosphonomethylglycine, prepared as in Example 1 above, there is added 4.6 grams (0.05 mole) of epichlorohydrin, and the solution is allowed to stir overnight at a temperature of 20°–25° C. The solution is left standing for several days with additions of sufficient sodium hydroxide solution to keep a phenolphthalein indicator strongly pink. An additional 2.0 grams of epichlorohydrin is added to complete the reaction, and the solution is allowed to stand for several more days with additions of sodium hydroxide as before. The solution is then rotoevaporated to dryness, and the residue is redried over potassium hydroxide pellets. The product, obtained as a white foamed glass, is the tetrasodium salt of N,N'-di(carboxymethyl)-N,N'-di(phosphonomethyl)-1,3-diamino-2-propanol.

EXAMPLE 3

To 2.7 grams (0.01 mole) of ethyl N-(phenoxyhydroxylphosphinylmethyl)glycinate in 10 ml. of water is added 0.8 gram (0.01 mole) of 50% aqueous sodium hydroxide. The solution is skaken and cooled in a pressure bottle. It is then treated with 0.5 gram (0.0114 mole) of ethylene oxide, sealed and allowed to warm to 20°–25° C., and then allowed to stand overnight. The resultant solution is rotoevaporated to dryness, and the residue is redried in vacuo over potassium hydroxide pellets. The product, obtained as a friable, white glass, is the monosodium salt of N-(2-hydroxyethyl)-N-(hydroxyphenoxyphosphinylmethyl)glycine in the hemihydrate form. Elemental analysis shows 41.09% carbon, 5.05% hydrogen and 9.70% phosphorus as against calculated values of 41.26%, 5.04% and 9.67% for $C_{11}H_{15}NaNO_6P \cdot \frac{1}{2} H_2O$.

EXAMPLE 4

To 8.5 grams (0.05 mole) of N-phosphonomethylglycine in 30 grams of water is added 0.8 grams of 50% aqueous sodium hydroxide. The solution is cooled and 3.6 grams (0.05 mole) of 1,2-butylene oxide is added. This solution is rotated in a capped bottle on a polymer wheel overnight. Additional amounts of 1,2-butylene oxide are added until no N-phosphonomethylglycine is detected in the solution, and unreacted 1,2-butylene oxide is then extracted with ethyl ether and benzene. The solution is rotoevaporated to dryness, and the residue is redried in vacuo over sodium hydroxide pellets. The product, obtained as brittle white foam, is the disodium salt of N-(2-hydroxy-1-butyl)-N-phosphonomethylglycine. Elemental analysis shows 30.68% carbon, 5.48% hydrogen, 4.70% nitrogen and 10.20% phosphorus as against calculated values of 29.49%, 4.95%, 4.91% and 10.86% for $C_7H_{14}NNa_2O_6P$.

EXAMPLE 5

To a slurry of 16.9 grams (0.1 mole) of N-phosphonomethylglycine in 50 ml. of water is added 16 grams (0.2 mole) of 50% aqueous sodium hydroxide. The hot solution is stirred and cooled to 35° C. in a flask equipped with a pressure-equalized dropping funnel and a dry-ice condenser vented to the atmosphere. To this solution is added 6.0 grams (0.1+ mole) of propylene oxide. The solution is stirred overnight. To complete the reaction, a 2.0 gram portion of propylene oxide is added, and the solution is stirred and then allowed to stand for several days. The solution is then rotoevaporated to dryness, and the solid is redried in vacuo over pellets of potassium hydroxide. The product, obtained as a brittle white foamed solid, is the disodium salt of N-(2-hydroxy-1-propyl)-N-phosphonomethylglycine. Elemental analysis shows 27.54% carbon, 4.63% hydrogen and 10.38% phosphorus as against calculated values of 26.58%, 4.46% and 11.42% for $C_6H_{12}NNa_2O_6P$.

EXAMPLE 6

To a solution of the disodium salt of N-phosphonomethylglycine, produced as in Example 1 above, is added 5.0 grams (0.114 mole) of ethylene oxide through a dry-ice condenser. The solution is allowed to stir overnight in a melting icebath and to stand for several days. To complete the reaction, successive 0.5 and 1.0 gram portions of ethylene oxide are added, allowing overnight reaction periods after each addition. The solution is then rotoevaporated to dryness, and the solid is redried over potassium hydroxide pellets. The product, obtained as a brittle white foam, is the disodium salt of N-(2-hydroxyethyl)-N-phosphonomethylglycine. Elemental analysis shows 22.96% carbon, 4.27% hydrogen and 11.31% phosphorus as against calculated values of 23.36%, 3.92% and 12.05% for $C_5H_{10}NNa_2O_6P$.

EXAMPLE 7

A solution of the disodium salt of N-phosphonomethylglycine is prepared as in Example 1. To 27.5 grams (0.0437 mole) of the solution is added 5.1 grams (0.05 mole) of ethyl glycidyl ether. The solution is diluted with 30 ml. water and 1 drop of Aliquat 336 phase-transfer catalyst solution is added. It is then rotated on a polymer wheel for 5 days, treated with 1.0 gram of ethyl glycidyl ether, rotated for 10 days, then warmed with charcoal and filtered to remove resinous material. The solution is then rotoevaporated to dryness, and the solid is redried over potassium hydroxide pellets at 100° C. and <1 mm. Hg. The product, obtained as a tan, brittle foamed glass, is the disodium salt of N-(3-ethoxy-2-hydroxy-1-propyl)-N-phosphonomethylglycine. Elemental analysis shows 31.15% carbon, 5.62% hydrogen and 8.87% phosphorus as against calculated values of 30.49%, 5.12% and 9.83% for $C_8H_{16}NNa_2O_7P$.

EXAMPLE 8

To a solution of 0.05 mole of the product of Example 5 above, is added 11.3 grams (0.1 mole) of 30% hydrogen peroxide. The solution is left standing for several days, then heated overnight at 40°-45° C. It is rotoevaporated to dryness at 40°-45° C. and <1 mm. Hg. and redried over potassium hydroxide for several days. The product, obtained as a brittle white foam, is the disodium salt of N-(2-hydroxypropyl)-N-phosphonomethylglycine,N-oxide.

EXAMPLE 9

To a solution of 0.05 mole of the product of Example 6 above, is added 11.3 grams (0.1 mole) of 30% hydrogen peroxide. The solution is left standing for 3 days at 20°-25° C., then heated overnight in an oven at 40°-45° C. It is rotoevaporated to dryness at 40°-45° C., and the solid is redried in vacuo over potassium hydroxide pellets for several days. The product, obtained as a brittle white foam, is the disodium salt of N-(2-hydroxyethyl)-N-phosphonomethylglycine,N-oxide.

EXAMPLE 10

To a solution of 10.0 grams of the product of Example 1 in 30 ml. of water, there is added 6.8 grams of 30% hydrogen peroxide. The solution is allowed to stand for a day at 20°-25° C., then heated overnight in an oven at 45° C., and finally rotoevaporated to dryness at a temperature below 50° C. The solid is redried in vacuo over potassium hydroxide pellets. The product, obtained as a brittle white foam, is the disodium salt of N-(2,3-dihydroxy-1-propyl)-N-phosphonomethylglycine,N-oxide.

EXAMPLE 11

To a solution of 10.0 grams of the product of Example 2 in 30 ml. of water, there is added 7.5 grams of 30% hydrogen peroxide. The solution is allowed to stand for a day at 20°-25° C., then heated overnight in an oven at 45° C., rotoevaporated to dryness at a temperature below 50° C., and the solid is redried in vacuo over potassium hydroxide pellets. The product, obtained as a brittle white foam, is the tetrasodium salt of N,N'-di(carboxymethyl)-N,N'-di(phosphonomethyl)-1,3-diamino-2-propanol,N,N'-dioxide.

EXAMPLE 12

To a solution of 18.6 grams (0.02 mole) of the disodium salt, prepared as in Example 1 above, there is added 4.7 grams of isopropyl glycidyl ether. A drop of Aliquat 336 phase-transfer catalyst solution is added, and the mixture is rotated on a polymer wheel for almost 6 days. An oil layer is extracted with ethyl ether, separated and discarded. A 12 gram portion of the remaining light yellow aqueous layer is filtered with charcoal, evaporated in a vacuum dessicator at <1 mm. and redried at 50° C. and <1 mm. The product, obtained as a colorless foamed glass, is the disodium salt of N-(3-isopropoxy-2-hydroxy-1-propyl)-N-phosphonomethylglycine. Elemental analysis shows 33.04% carbon, 5.77% hydrogen, 3.84% nitrogen and 8.47% phosphorus as against calculated values of 32.84%, 5.51%, 4.25% and 9.41% for $C_9H_{18}NNa_2O_7P$.

EXAMPLE 13

To a solution of 18.7 grams (0.02 mole) of the disodium salt, prepared as in Example 1 above, there is added 2.7 grams (0.03 mole) of methyl glycidyl ether. The mixture is rotated on a polymer wheel for about 10 days. The clear solution is extracted three times with ethyl ether, and residual ether is blown out with nitrogen. The product, obtained in a light yellow aqueous solution, is identified by nuclear magnetic resonance as the disodium salt of N-(3-methoxy-2-hydroxy-1-propyl)-N-phosphonomethylglycine.

EXAMPLE 14

To a solution of 18.7 grams (0.02 mole) of the disodium salt, prepared as in Example 1 above, there is added 3.4 grams (0.03 mole) of allyl glycidyl ether, and the mixture is rotated on a polymer wheel for about 10 days. An oil layer is extracted twice with ethyl ether, and residual ether is blown out with nitrogen. The remaining colorless solution is passed through a column of ion exchange resin in the acid form. Cuts 24-50 are collected, and a portion of these cuts is neutralized with 50% sodium hydroxide. The product, obtained in a colorless aqueous solution, is identified by nuclear magnetic resonance as the disodium salt of N-(3-allyloxy-2-hydroxy-1-propyl)-N-phosphonomethylglycine.

The post-emergence herbicidal activity of various compounds of this invention is demonstrated as follows. The active ingredients are applied in spray form to 14-21 day-old specimens of various plant species. The spray, a water or organic solvent-water solution containing active ingredient and a surfactant (35 parts butylamine salt of dodecylbenzenesulfonic acid and 65 parts tall oil condensed with ethylene oxide in the ratio of 11 moles ethylene oxide to 1 mole tall oil), is applied to the plants in different sets of pans at several rates (kg per hectare) of active ingredient. The treated plants are placed in a greenhouse and the effects are observed and recorded after approximately 2 weeks or approximately 4 weeks. The data is given in Tables I and II.

The post-emergence herbicidal activity index used in Table I and II is as follows:

| Plant Response | Index |
|---|---|
| 0-24% Injury | 0 |
| 25-49% Injury | 1 |
| 50-74% Injury | 2 |
| 75-99% Injury | 3 |
| All Killed | 4 |
| Species not present at time of treatment | * |

In said Tables, WAT indicates weeks after treatment, and the plant species treated are each represented by a code letter as follows:

A—Canada Thistle
B—Cocklebur
C—Velvet Leaf
D—Morning Glory
E—Lambsquarter
F—Smartweed
G—Nutsedge
H—Quackgrass
I—Johnson Grass
J—Downy Brome
K—Barnyard Grass
L—Soybean
M—Sugar Beet
N—Wheat
O—Rice
P—Sorghum
Q—Wild Buckwheat
R—Hemp Sesbania
S—Panicum Spp
T—Crabgrass

TABLE I

| Compound | WAT | kg/h | A | B | C | D | E | F | G | H | I | J | K |
|---|---|---|---|---|---|---|---|---|---|---|---|---|---|
| 1 | 2 | 11.2 | 0 | 0 | 0 | 0 | 3 | 0 | 0 | 0 | 0 | 0 | 0 |
| 2 | 2 | 11.2 | 2 | 0 | 0 | 1 | 3 | 0 | 1 | 0 | 0 | 0 | 2 |
|   | 4 | 11.2 | 3 | 1 | 0 | 2 | 4 | 0 | 1 | 1 | 1 | 1 | 2 |
|   | 2 | 4.48 | 1 | * | 0 | 0 | 1 | 1 | 1 | 1 | 1 | 1 | 2 |
|   | 4 | 4.48 | 1 | * | 0 | 0 | 1 | 1 | 0 | 0 | 0 | 0 | 1 |
| 3 | 2 | 11.2 | 2 | 2 | 1 | 1 | 3 | 2 | 0 | 0 | 1 | 1 | 1 |
|   | 4 | 11.2 | 2 | 2 | 1 | 1 | 3 | 2 | 1 | 0 | 3 | 1 | 3 |
|   | 2 | 5.6 | 1 | 2 | 1 | 1 | 1 | 1 | 0 | 0 | 0 | 0 | 1 |
|   | 4 | 5.6 | 1 | 1 | 1 | 1 | 1 | 2 | 0 | 1 | 1 | 1 | 2 |
| 4 | 2 | 11.2 | 1 | 0 | 0 | 0 | 1 | 0 | 0 | 0 | 0 | 0 | 0 |
|   | 4 | 11.2 | 0 | 0 | 0 | 0 | 0 | 0 | 0 | 0 | 0 | 0 | 0 |
|   | 2 | 5.6 | 1 | 0 | 0 | 1 | 0 | 0 | 0 | 0 | 0 | 0 | 0 |
|   | 4 | 5.6 | 0 | 0 | 0 | 0 | 0 | 0 | 0 | 0 | 0 | 0 | 0 |
| 5 | 2 | 11.2 | 1 | * | 1 | 1 | 1 | 1 | 1 | 0 | 1 | 0 | 2 |
|   | 4 | 11.2 | 2 | * | 1 | 2 | 3 | 1 | 2 | 1 | 2 | 0 | 2 |
|   | 2 | 4.48 | 1 | 1 | 1 | 1 | 1 | 0 | 0 | 0 | * | 0 | 1 |
| 6 | 2 | 11.2 | 1 | * | 1 | 2 | 3 | 2 | 1 | 2 | 0 | 1 | 3 |
|   | 4 | 11.2 | 3 | * | 2 | 3 | 3 | 2 | 2 | 3 | 1 | 2 | 3 |
|   | 2 | 4.48 | 1 | * | 1 | 2 | 1 | 2 | 0 | 0 | 0 | 1 | 3 |
|   | 4 | 4.48 | 1 | * | 2 | 2 | 2 | 2 | 1 | 0 | 0 | 3 | 4 |
| 7 | 2 | 11.2 | 1 | 2 | 1 | 1 | 2 | 3 | 1 | 3 | 2 | 2 | 3 |
|   | 4 | 11.2 | 3 | 3 | 1 | 1 | 2 | 4 | 2 | 4 | 4 | 2 | 4 |
|   | 2 | 5.6 | 1 | 1 | 0 | 1 | 2 | 2 | 0 | 1 | 0 | 0 | 1 |
|   | 4 | 5.6 | 2 | 1 | 0 | 1 | 2 | 2 | 1 | 1 | 0 | 0 | 1 |
| 8 | 2 | 11.2 | 1 | * | 0 | 1 | 2 | 0 | 1 | 0 | 1 | 0 | 2 |
|   | 4 | 11.2 | 1 | * | 1 | 2 | 3 | 0 | 2 | 2 | 2 | 0 | 3 |
| 9 | 2 | 11.2 | 1 | * | 0 | 0 | 0 | * | 1 | 0 | 0 | 0 | 1 |
| 10 | 2 | 11.2 | 1 | 1 | 0 | 1 | 3 | 1 | 0 | 0 | 1 | 0 | 1 |
|   | 4 | 11.2 | 1 | 1 | 0 | 1 | 4 | 1 | 0 | 0 | 1 | 0 | 1 |
| 11 | 2 | 11.2 | 1 | 1 | 1 | 1 | 3 | 0 | 1 | 0 | 0 | 0 | 0 |

TABLE I-continued

| Compound | WAT | kg/h | A | B | C | D | E | F | G | H | I | J | K |
|---|---|---|---|---|---|---|---|---|---|---|---|---|---|
| | 4 | 11.2 | 1 | 1 | 1 | 1 | 3 | 0 | 1 | 0 | 0 | 0 | 0 |
| 12 | 2 | 11.2 | 0 | 1 | 1 | 1 | 1 | 1 | 1 | 1 | 0 | 0 | 2 |
| | 4 | 11.2 | 1 | 1 | 1 | 1 | 2 | 2 | 1 | 1 | 0 | 1 | 2 |
| | 2 | 5.6 | 1 | 1 | 0 | 1 | 0 | 1 | 0 | 1 | 0 | 0 | 1 |
| | 4 | 5.6 | 1 | 1 | 0 | 1 | 1 | 1 | 1 | 1 | 0 | 0 | 2 |
| 13 | 2 | 11.2 | 1 | 3 | 2 | 1 | 3 | 3 | 1 | 1 | 2 | 2 | 3 |
| | 4 | 11.2 | 2 | 3 | 2 | 2 | 4 | 4 | 1 | 2 | 2 | 2 | 3 |
| | 2 | 5.6 | 1 | 1 | 1 | 1 | 3 | 3 | 1 | 0 | 0 | 1 | 2 |
| | 4 | 5.6 | 1 | 2 | 1 | 2 | 4 | 3 | 0 | 1 | 0 | 3 | 2 |
| 14 | 2 | 11.2 | 1 | 1 | 1 | 1 | 1 | 1 | 1 | 0 | 1 | 0 | 1 |
| | 4 | 11.2 | 1 | 2 | 0 | 1 | 2 | 0 | 1 | 0 | 1 | 0 | 2 |
| | 2 | 5.6 | 1 | 1 | 0 | 1 | 1 | 1 | 1 | 0 | 0 | 0 | 1 |
| | 4 | 5.6 | 0 | 1 | 0 | 1 | 1 | 1 | 0 | 0 | 0 | 0 | 1 |

TABLE II

| Compound | WAT | kg/h | L | M | N | O | P | B | Q | D | R | E | F | C | J | S | K | T |
|---|---|---|---|---|---|---|---|---|---|---|---|---|---|---|---|---|---|---|
| 3 | 2 | 5.6 | 2 | 3 | 4 | 1 | 3 | 2 | 1 | 2 | 2 | 4 | 3 | 2 | 2 | 3 | 3 | 4 |
| | 4 | 5.6 | 2 | 3 | 4 | 2 | 3 | 2 | 1 | 2 | 2 | 4 | 4 | 2 | 2 | 4 | 3 | 4 |
| | 2 | 1.12 | 1 | 1 | 1 | 1 | 2 | 2 | 1 | 1 | 2 | 2 | 1 | 1 | 0 | 3 | 1 | 3 |
| | 4 | 1.12 | 1 | 1 | 1 | 1 | 2 | 2 | 2 | 2 | 1 | 2 | 1 | 1 | 0 | 4 | 1 | 3 |
| 6 | 2 | 4.48 | 0 | 4 | 1 | 0 | 2 | 1 | 1 | 2 | 3 | 3 | 2 | 2 | 2 | 4 | 2 | 3 |
| | 4 | 4.48 | 0 | 4 | 1 | 0 | 3 | 1 | 0 | 1 | 3 | 4 | 2 | 2 | 3 | 4 | 3 | 3 |
| | 2 | 1.12 | 0 | 0 | 0 | 0 | 0 | 0 | 0 | 0 | 0 | 1 | 1 | 0 | 0 | 1 | 0 | 3 |
| 7 | 2 | 5.6 | 2 | 2 | 0 | 0 | 2 | 2 | 1 | 1 | 1 | 4 | 3 | 1 | 3 | 3 | 3 | 4 |
| | 4 | 5.6 | 2 | 3 | 1 | 1 | 3 | 2 | 1 | 2 | 1 | 4 | 4 | 1 | 3 | 3 | 3 | 4 |
| | 2 | 1.12 | 1 | 0 | 1 | 0 | 1 | 1 | 0 | 1 | 1 | 2 | 2 | 0 | 1 | 1 | 1 | 2 |
| | 4 | 1.12 | 1 | 1 | 1 | 0 | 1 | 1 | 0 | 1 | 1 | 2 | 2 | 0 | 0 | 2 | 0 | 3 |
| 8 | 2 | 4.48 | 0 | 0 | 1 | 1 | 1 | 1 | 0 | 0 | 1 | 1 | 1 | 0 | 2 | 1 | 1 | 1 |
| | 2 | 1.12 | 0 | 0 | 1 | 0 | 0 | 0 | 0 | 0 | 1 | 1 | 0 | 0 | 0 | 0 | 0 | 1 |
| 13 | 2 | 5.6 | 0 | 0 | 2 | 1 | 1 | 2 | 1 | 2 | 2 | 4 | 3 | 1 | 1 | 2 | 2 | 3 |
| | 4 | 5.6 | 0 | 1 | 2 | 1 | 2 | 2 | 1 | 2 | 1 | 4 | 3 | 2 | 2 | 3 | 3 | 4 |
| | 2 | 1.12 | 0 | 0 | 0 | 1 | 0 | 0 | 0 | 1 | 2 | 1 | 1 | 0 | 0 | 3 | 1 | 2 |
| | 4 | 1.12 | 0 | 1 | 1 | 0 | 1 | 0 | 0 | 1 | 1 | 2 | 2 | 0 | 0 | 3 | 1 | 2 |

The herbicidal compositions, including concentrates which require dilution prior to application to the plants, of this invention contain from 5 to 95 parts by weight of at least one active ingredient and from 5 to 95 parts by weight of an adjuvant in liquid or solid form, for example, from about 0.25 to 25 parts by weight of wetting agent, from about 0.25 to 25 parts by weight of dispersant and from 4.5 to about 94.5 parts by weight of inert liquid extender, e.g., water, all parts being by weight of the total composition. Where required from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isethionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acyl) taurates.

Water dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible powder of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

Although compositions of this invention can also contain other additaments, for example, fertilizers, phytotoxicant and plant growth regulators, pesticides and the like used as adjuvants or in combination with any of the above-described adjuvants, it is preferred to employ the compositions of this invention alone with sequential treatments with the other phytotoxicants, fertilizers and the like for maximum effect. For example, the field could be sprayed with a composition of this invention either before or after being treated with fertilizers other phytotoxicants and the like. The compositions of this invention can also be admixed with the other materials, e.g., fertilizers, other phytotoxicants, etc., and applied in a single application. Chemicals useful in combination with the active ingredients of this invention either simultaneously or sequentially include, for example, triazines, ureas, carbamates, acetamides, acetanilides, uracils, acetic acids, phenols, thiolcarbamates, triazoles, benzoic acids, nitriles and the like.

Fertilizers useful in combination with the active ingredients include, for example, ammonium nitrate, urea, potash, and superphosphate.

When operating in accordance with the present invention effective amounts of the glycines are applied to above-ground portions of plants. The application of liquid and particulate solid herbicidal compositions to above-ground portions of plants can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by spraying the compositions on the aquatic plants in the area where control of the aquatic plants is desired.

The application of an effective amount of the compounds of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although the invention is described with respect to specific modifications, the details thereof are not to be construed as limitations except to the extent indicated in the following claims.

What is claimed is:

1. A compound of the formula

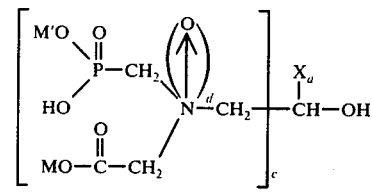

wherein X is selected from hydroxymethyl, lower alkoxymethyl and lower alkenoxymethyl, M is selected from hydrogen, lower alkyl and alkali metal, M' is selected from hydrogen, lower alkyl, phenyl and alkali metal, $a$ is zero or one, $c$ is one or two, and $d$ is zero or one, provided that the sum of $a + c$ must equal two.

2. A compound as defined in claim 1 wherein M and M' are each alkali metal.

3. A compound as defined in claim 1 wherein $d$ is one.

4. A compound as defined in claim 1 wherein $d$ is zero and $c$ is two.

5. A compound as defined in claim 1 wherein $a$ and $c$ are one, and X is lower alkoxymethyl.

6. A compound as defined in claim 1 wherein $a$ and $c$ are one, and X is lower alkenoxymethyl.

7. A compound as defined in claim 1 wherein $a$ and $c$ are one, and X is hydroxymethyl.

8. A compound as defined in claim 2 wherein said alkali metal is sodium.

9. A phytotoxic composition comprising an inert adjuvant and a herbicidally effective amount of a compound of claim 1.

10. A phytotoxic composition comprising an inert adjuvant and a herbicidally effective amount of a compound of claim 2.

11. A phytotoxic composition comprising an inert adjuvant and a herbicidally effective amount of a compound of claim 3.

12. A phytotoxic composition comprising an inert adjuvant and a herbicidally effective amount of a compound of claim 4.

13. A phytotoxic composition comprising an inert adjuvant and a herbicidally effective amount of a compound of claim 5.

14. A phytotoxic composition comprising an inert adjuvant and a herbicidally effective amount of a compound of claim 6.

15. A phytotoxic composition comprising an inert adjuvant and a herbicidally effective amount of a compound of claim 7.

16. A phytotoxic composition comprising an inert adjuvant and a herbicidally effective amount of a compound of claim 8.

* * * * *